(12) United States Patent
Wang et al.

(10) Patent No.: US 9,097,616 B2
(45) Date of Patent: Aug. 4, 2015

(54) APPARATUS FOR COLLECTING MATERIAL TO BE SPECTRALLY ANALYZED

(71) Applicant: Hewlett-Packard Development Company, L.P., Houston, TX (US)

(72) Inventors: Shih-Yuan Wang, Palo Alto, CA (US); Huei Pei Kuo, Cupertino, CA (US); Zhiyong Li, Foster City, CA (US); Gary Gibson, Palo Alto, CA (US)

(73) Assignee: HEWLETT-PACKARD DEVELOPMENT COMPANY, L.P., Houston, TX (US)

( * ) Notice: Subject to any disclaimer, the term of this patent is extended or adjusted under 35 U.S.C. 154(b) by 4 days.

(21) Appl. No.: 13/750,848

(22) Filed: Jan. 25, 2013

(65) Prior Publication Data
US 2014/0211206 A1     Jul. 31, 2014

(51) Int. Cl.
| G01J 3/44 | (2006.01) |
| G01N 1/00 | (2006.01) |
| A61B 5/00 | (2006.01) |
| A61B 5/1459 | (2006.01) |
| G01N 21/65 | (2006.01) |
| G01N 1/02 | (2006.01) |

(52) U.S. Cl.
CPC .............. *G01N 1/00* (2013.01); *A61B 5/0075* (2013.01); *A61B 5/1459* (2013.01); *A61B 5/6847* (2013.01); *G01N 21/658* (2013.01); *A61B 2562/028* (2013.01); *A61B 2562/0285* (2013.01); *G01N 1/02* (2013.01); *Y10T 29/49826* (2015.01)

(58) Field of Classification Search
USPC .............................................. 356/301, 72–73
See application file for complete search history.

(56) References Cited

U.S. PATENT DOCUMENTS

| 5,128,882 | A  | * | 7/1992 | Cooper et al. .................. 702/11 |
| 6,776,962 | B1 | * | 8/2004 | Boss et al. ................. 422/82.11 |
| 7,940,387 | B2 |   | 5/2011 | Dluhy et al. |
| 2005/0195393 | A1 | * | 9/2005 | Karanassios .................. 356/316 |
| 2007/0232902 | A1 | * | 10/2007 | Teramura ...................... 600/425 |
| 2010/0087723 | A1 |   | 4/2010 | Van Duyne et al. |
| 2010/0089383 | A1 | * | 4/2010 | Cowles ....................... 126/360.1 |
| 2013/0041233 | A1 | * | 2/2013 | Yadlowsky et al. ........... 600/249 |

FOREIGN PATENT DOCUMENTS

CN            202078585           12/2011

OTHER PUBLICATIONS

Dhawan, A. et al., Nano-engineered Surface-enhanced Raman Scattering (SERS) Substrates with Patterned Structures on the Distal End of Optical Fibers, (Research Paper), Feb. 7, 2008, vol. 6869.

(Continued)

*Primary Examiner* — Abdullahi Nur
(74) *Attorney, Agent, or Firm* — Mannava & Kang, P.C.

(57) ABSTRACT

According to an example, an apparatus for collecting a material to be spectrally analyzed includes a body having a first end and a second end, in which the body is elongated along a first axis from the first end to the second end. The body also includes a hole having an opening formed in an external surface of the body at a location between the first end and the second end and extending at least partially through the body at an angle with respect to the first axis. The body further includes a plurality of surface-enhanced spectroscopy (SES) elements positioned inside the body.

14 Claims, 9 Drawing Sheets

(56) References Cited

OTHER PUBLICATIONS

Stokes, D.L. et al., Development of an Integrated Single-fiber SERS Sensor, (Web Page), Sep. 10, 2000, pp. 28-36, vol. 69, No. 1-2. http://www.sciencedirect.com/science/article/pii/S0925400500002914.

Du, Henry, "Fiber-Optic Based SERS Probes and Optofluidic Devices", Department of chemical engineering and materials schaefer school of engineering & science, May 18, 2010.

Ferrante Do Amaral, Carlos E., et al., "Current development in non0invasive glucose monitoring", Medical Engineering & Physics, Elsevier, Jun. 12, 2007.

Santos, Luis F., et al., "Fiber-Optic Probes for in Vivo Raman Spectroscopy in the High-Wavenumber Region", Technical Notes, 2005.

Gu, Claire, et al., "Fiber-Based Sensors: Surface-enhanced Raman sensors improves detection of dangerous agents", Laser Focus World, Download Date: Jun. 12, 2012.

Kurihara, Kazuyoshi, et al., "Fiber-optic conical microsensors for surface plasmon resonance using chemically etched single-mode fiber" Elsevier, Jul. 19, 2004.

Dhawan A., et al., "Focused in beam fabrication of metallic nanostructures on end faces of optical fibers for chemical sensing applications", Dec. 1, 2008.

Ma, Ke, et al., "In Vivo, Transculaneous Glucose Sensing Using Surface-Enhanced Spatially Offset Raman Spectroscopy: Multiple Rats, Improved Hypoglycemic Accuracy, Low Incident Power, and Continuous Monitoring for Greater than 17 Days" Analytical Chemistry, Oct. 18, 2011.

Yang, Xuan, et al., "Hollow-Core Photonic Crystal Fibers for Surface-Enhanced Raman Scattering Probes", Hindawi Publishing Corporation, Feb. 8, 2011.

U.S., Dinish, et al, "Nanosphere Templated Optical Fiber for In-Vivo SERS Sensing Applications", 2010.

White, Daniel J., et al., "Nanostructured optical fibre for chemical sensing using surfaceenhanced Raman scattering", Jul. 2006.

"Sensor pins and microneedles", Materialstoday, vol. 15, No. 1-2, Jan.-Feb. 2012.

* cited by examiner

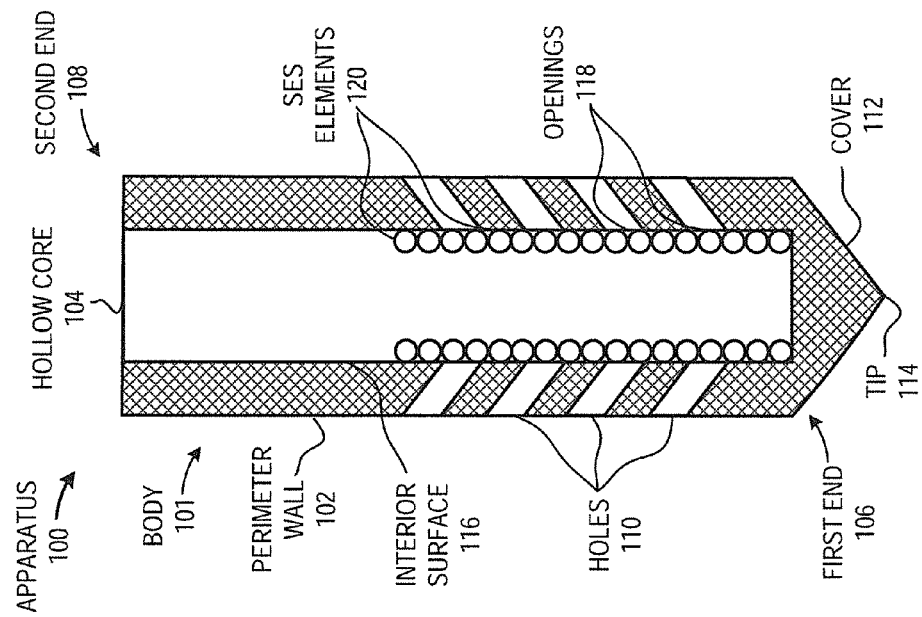
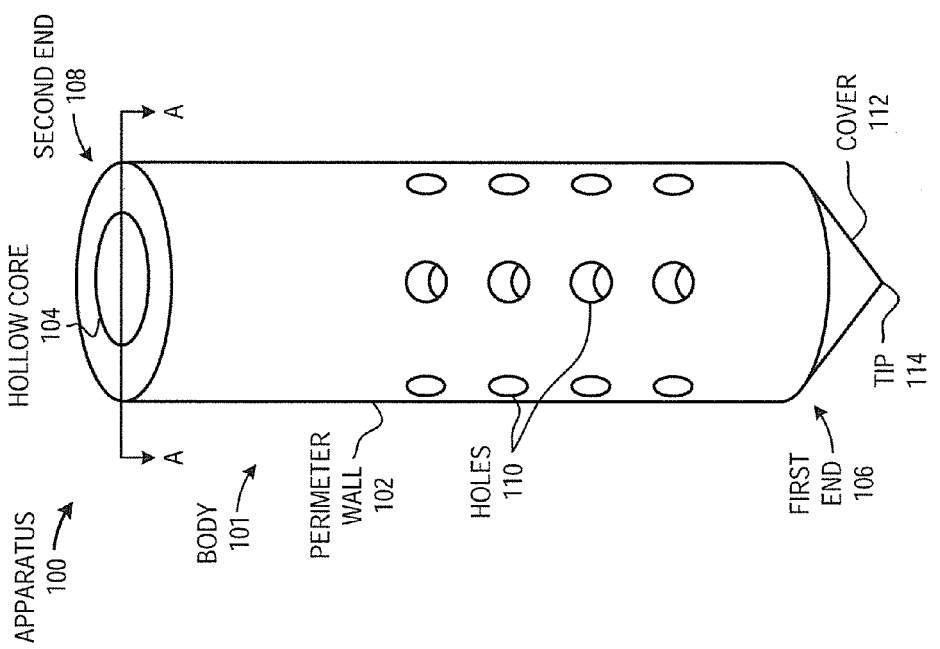

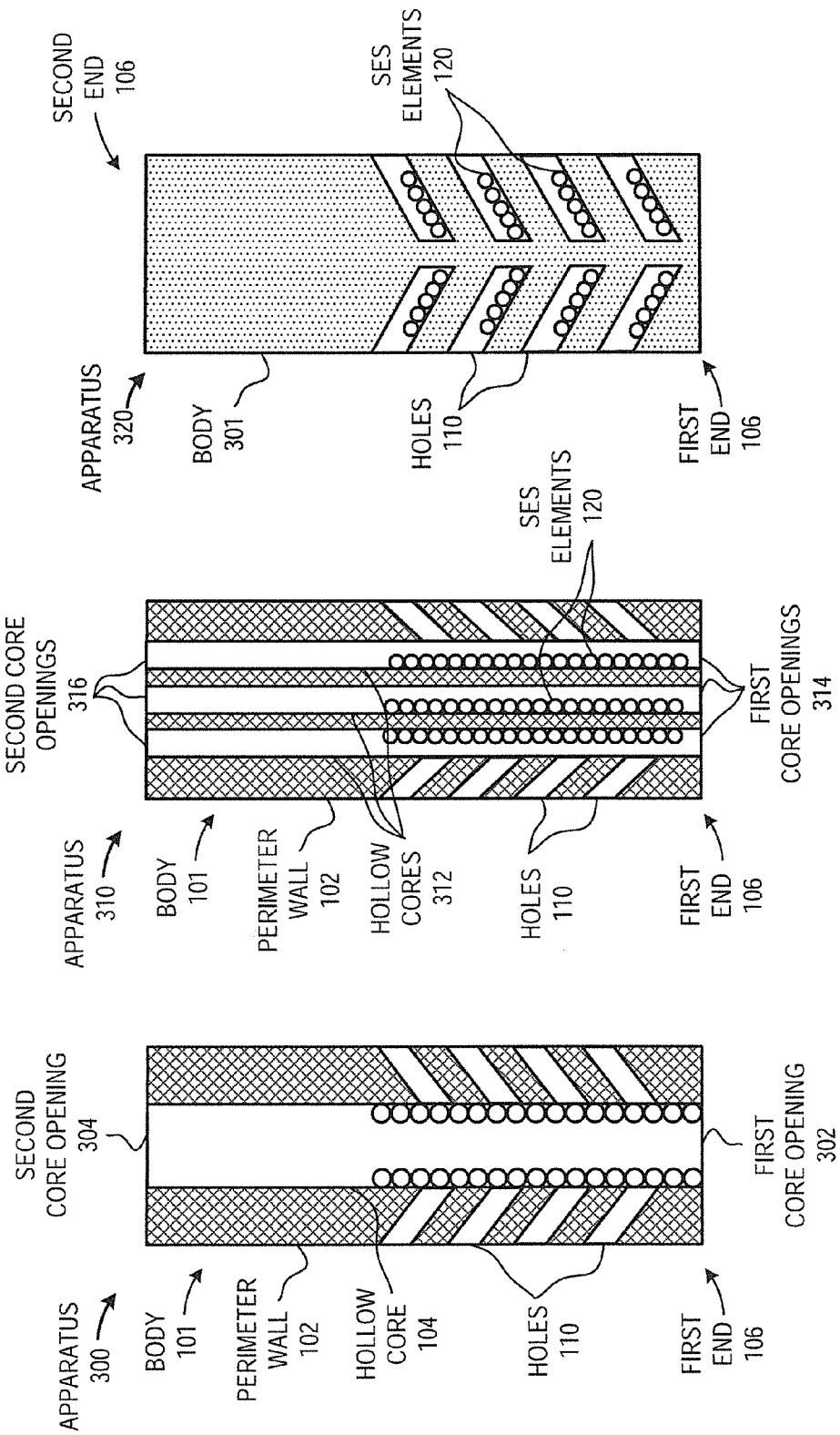

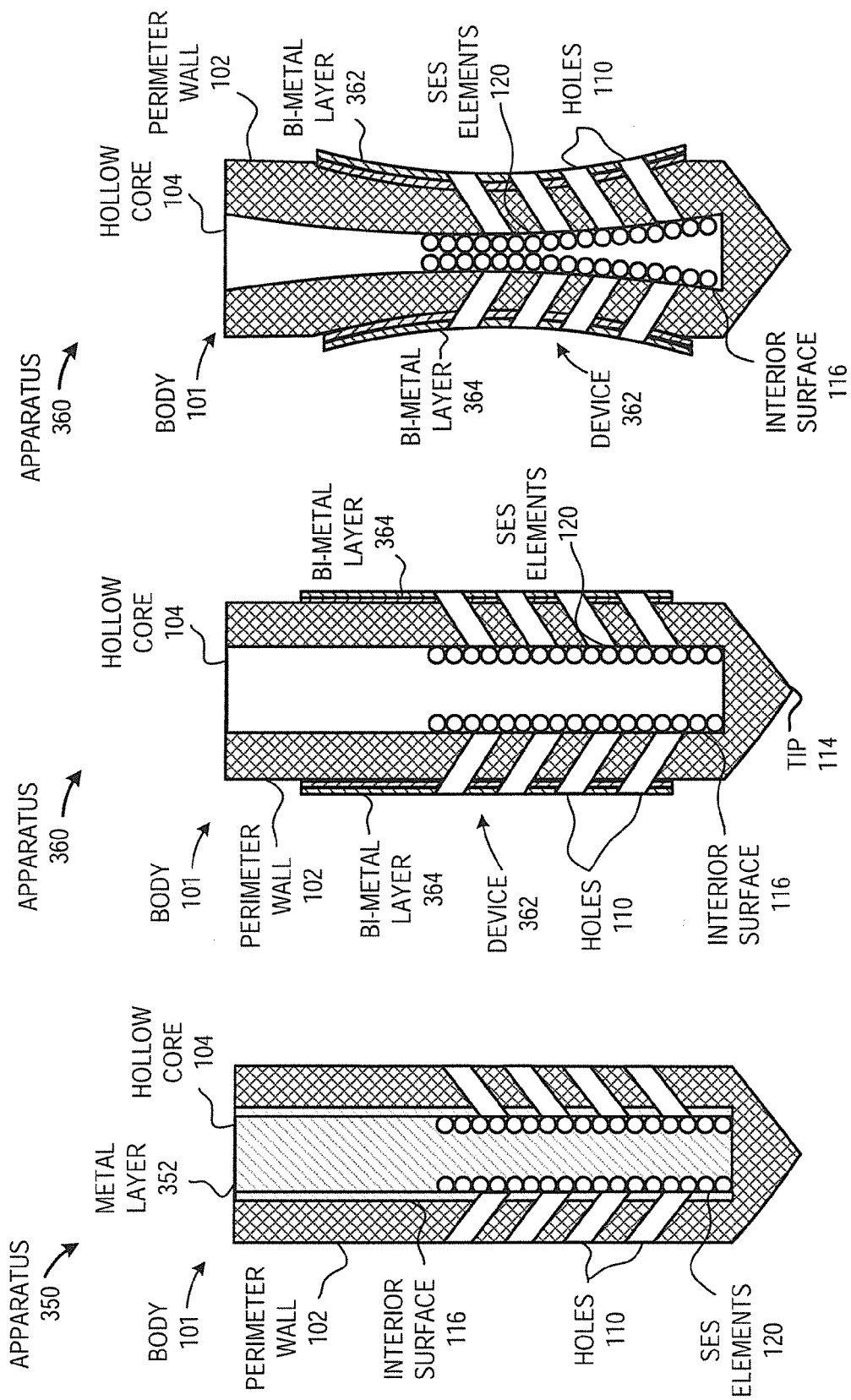

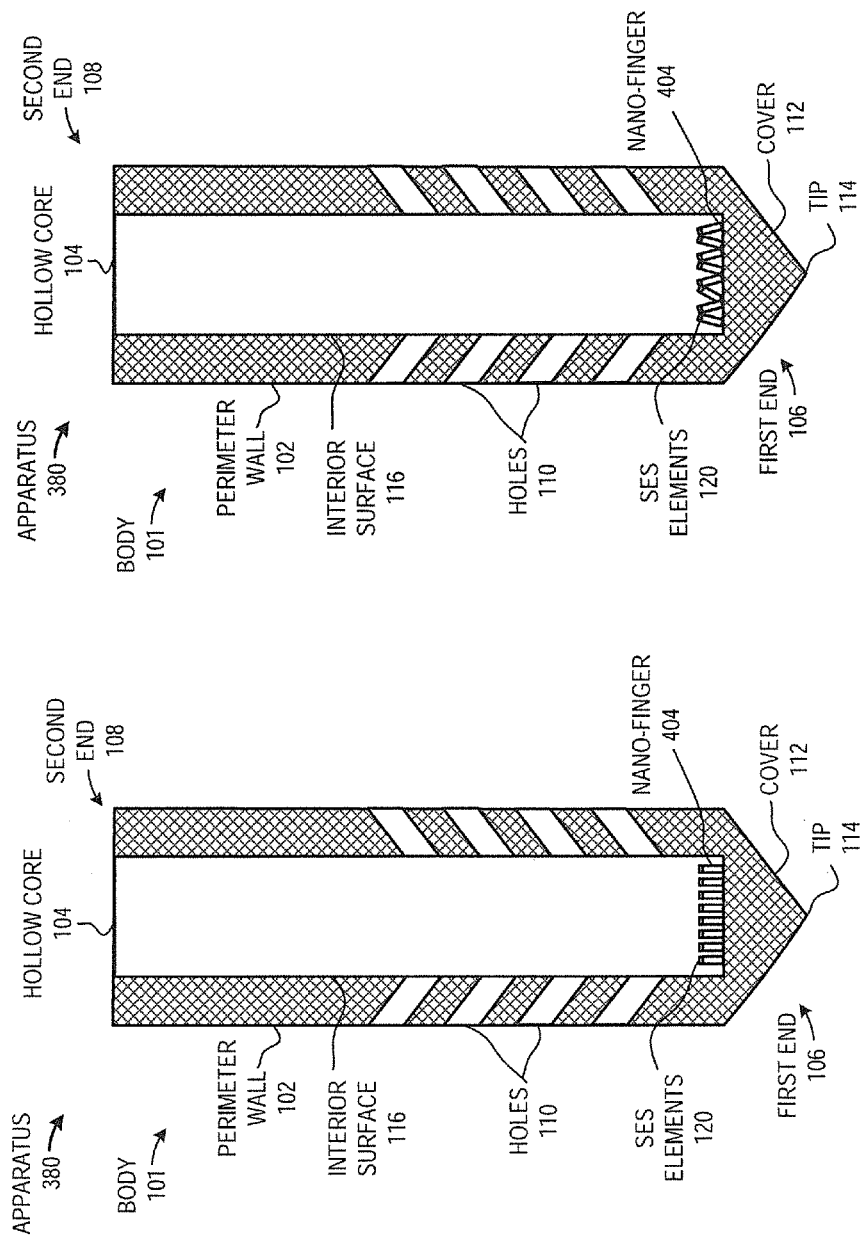

APPARATUS FOR COLLECTING MATERIAL TO BE SPECTRALLY ANALYZED

BACKGROUND

In surface-enhanced spectroscopy (SES), such as surface-enhanced Raman spectroscopy (SERS), vibrationally excitable levels of an analyte are probed. The energy of a photon can shift by an amount equal to that of the vibrational level excited by the photon (Raman scattering). A Raman spectrum, which consists of a wavelength distribution of bands corresponding to molecular vibrations specific to the analyte being probed, may be detected to identify the analyte. In SERS, the analyte molecules are in close proximity, for instance, less than tens of nanometers, to metal nano-particles that may be or may not be coated with a dielectric, such as silicon dioxide, silicon nitride, and a polymer, that, once excited by light, set up plasmon modes, which create near fields around the metal nano-particles. These fields can couple to analyte molecules in the near field regions. As a result, concentration of the incident light occurs at close vicinity to the nano-particles, enhancing the Raman scattering from the analyte molecules.

SERS has recently been performed to probe materials beneath a surface through insertion of an optical fiber having a hollow core containing metal nanoparticles through the surface. Conventional optical fibers have openings at distal ends of the optical fibers for the material to be collected into the hollow core and onto the metal nanoparticles. SERS is then performed on the collected material through application of excitation light onto the metal nanoparticles and materials and detection of Raman scattered light from the materials.

BRIEF DESCRIPTION OF THE DRAWINGS

Features of the present disclosure are illustrated by way of example and not limited in the following figure(s), in which like numerals indicate like elements, in which:

FIG. 1A shows a perspective view of an apparatus for collecting a material to be spectrally analyzed, according to an example of the present disclosure;

FIG. 1B shows a cross-sectional side view of the apparatus taken along lines A-A in FIG. 1A, according to an example of the present disclosure;

FIGS. 3A-3C, respectively show cross-sectional side views of an apparatus for collecting a material to be spectrally analyzed, according to examples of the present disclosure;

FIGS. 3F-3I, respectively show cross-sectional side views of an apparatus for collecting a material to be spectrally analyzed, according to examples of the present disclosure;

FIGS. 4D and 4E, respectively show cross-sectional side views of an apparatus for collecting a material to be spectrally analyzed, according to another example of the present disclosure.

DETAILED DESCRIPTION

Figure 2:
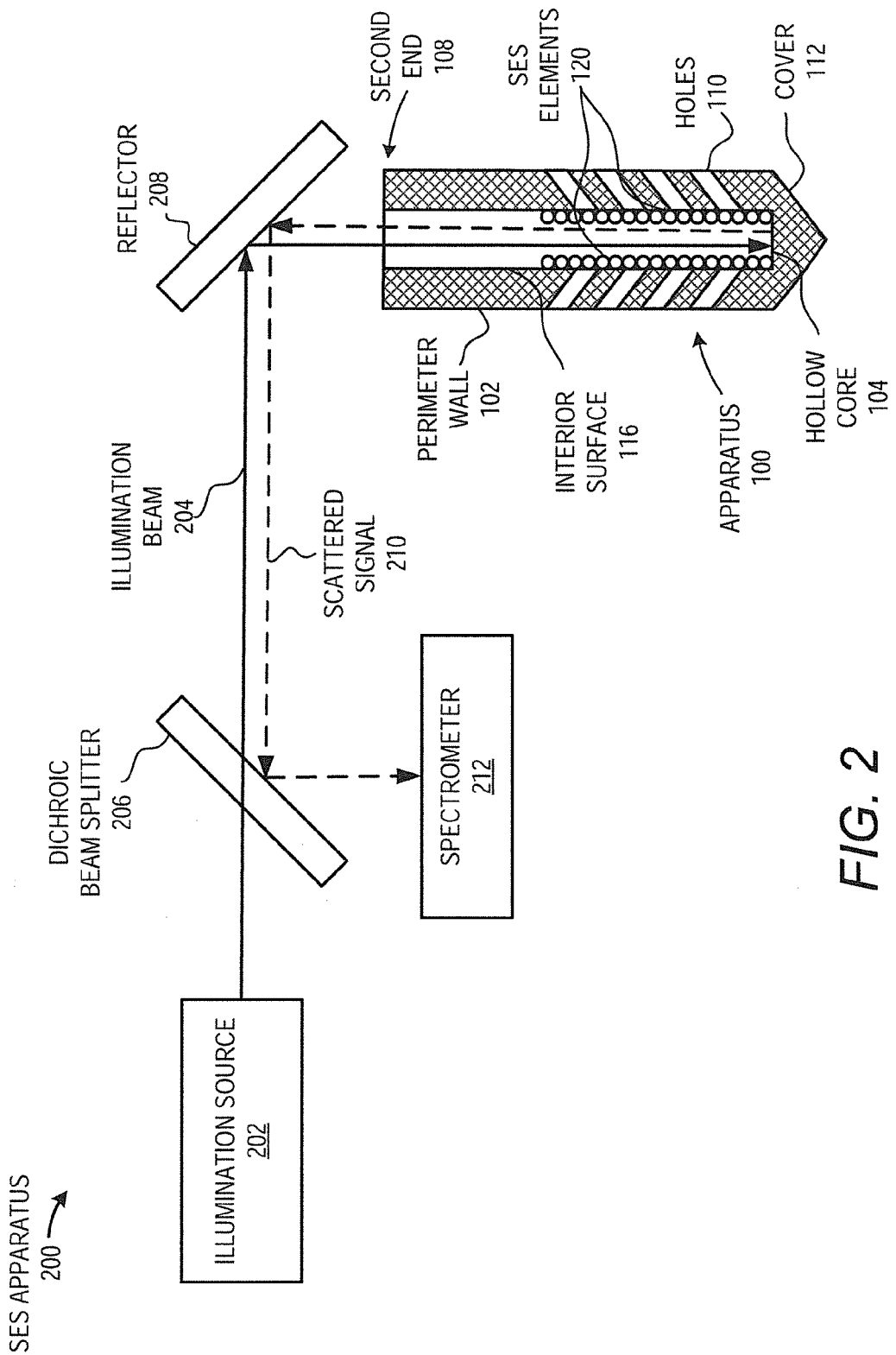
FIG. 2 shows a diagram of an apparatus for performing SES, according to an example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared, near infrared, and ultra-violet portions of the electromagnetic spectrum.

Disclosed herein are an apparatus for collecting a material to be spectrally analyzed and a method for fabricating the apparatus. Also disclosed herein is an apparatus for performing spectroscopy that may implement the material collecting apparatus. The material collecting apparatus disclosed herein may include a body having a first end and a second end, in which the body is elongated along a first axis from the first end to the second end. In addition, a hole having an opening formed in an external surface of the body at a location between the first end and the second end and extending at least partially through the body at an angle with respect to the first axis may be formed in the body. Moreover, a plurality of surface-enhanced spectroscopy (SES) elements may be positioned inside the body.

The material collecting apparatus disclosed herein may be fabricated to be inserted into an item of interest, e.g., a specimen, such as a human, an animal, an insect, a plant, a non-living item, etc. By way of particular example, the item of interest may be a living being and the analyte may be a blood sample, an interstitial fluid sample, a tissue sample, etc. As another example, the item of interest may be a fluid, such as milk. In this example, the analyte may be the fluid itself or molecules, species, compounds, etc., contained in the fluid. As a yet further example, the item of interest may be a fruit, a processed food, etc. Again, the analyte in this example may be a biological and/or chemical species contained beneath the surface of an item of interest.

The material collecting apparatus may be elongated along one axis and may be inserted into the item of interest in a direction that is parallel to the axis. In addition, the material collecting apparatus may collect sample material from the item of interest through the hole, which may traverse the material collecting apparatus in a direction that is substantially transverse to the direction in which the material collecting apparatus is to be inserted into the item of interest. In one regard, therefore, the hole may not be as likely to become clogged by material during insertion of the material collecting apparatus disclosed herein into the item of interest. As such, the material collecting apparatus disclosed herein may afford greater probability of sufficient material to be collected into the apparatus for spectral analysis to be performed on the material.

The material collecting apparatus disclosed herein may be implemented to perform spectroscopy, which is also equivalently referred herein as surface-enhanced spectroscopy (SES), to detect a molecule in an analyte sample collected in the apparatus with a relatively high level of sensitivity. As an example, the material collecting apparatus disclosed herein may be implemented to perform spectroscopy on the collected material while the apparatus is inserted into the item of interest. In another example, the material collecting apparatus disclosed herein may be implemented to perform spectroscopy on the collected material following removal of the apparatus from the item of interest.

With reference first to FIG. 1A, there is shown a perspective view of an apparatus 100 for collecting a material to be spectrally analyzed, according to an example. It should be understood that the apparatus 100 depicted in FIG. 1A may include additional components and that some of the components described herein may be removed and/or modified without departing from a scope of the apparatus 100. It should also be understood that the components depicted in FIG. 1A are not drawn to scale and thus, the components may have different relative sizes with respect to each other than as shown therein.

As shown in FIG. 1A, the apparatus 100 may include a body 101, which in this example includes a perimeter wall 102 surrounding a hollow core 104, in which the hollow core 104 may be formed by an interior surface of the perimeter wall 102. The perimeter wall 102 may also include a first end 106 and a second end 108, in which the second end 108 is positioned at an opposite end of the perimeter wall 102 from the first end 106. In addition, the perimeter wall 102 may extend along an axis from the first end 106 to the second end 108.

The perimeter wall 102 may be formed of any reasonably suitable type of material that is of sufficient strength to maintain its shape during insertion of the apparatus 100 into an item of interest. The perimeter wall 102 may be formed of plastic, silver, titanium, composite materials, polymers, silicon, etc. The perimeter wall 102 may also be formed of other materials, such as materials that may be toxic to a specimen.

By way of particular example, the perimeter wall 102 may be a hollow core optical fiber, which may include a photonic crystal or a holey fiber. In this example, the perimeter wall 102 may be an optically transparent material that is surrounded by a cladding (not shown) along the longitudinal axis of the perimeter wall 102. As another example, the perimeter wall 102 may be formed of an optically reflective material and/or is fabricated such that the interior surface of the perimeter wall 102 is optically reflective. For instance, the interior surface of the perimeter wall 102 may be coated with at least one of a metal, such as gold, silver, TiN (titanium nitride), ZnO (zinc oxide), ITO (indium tin oxide), etc., a protective coating of dielectric material, Bragg layers, etc., to be reflective.

According to an example, the apparatus 100 may have a length that is in the range of about 1 millimeter to 3 centimeters and the body 101 has a maximum diameter across its length (i.e., perpendicular to the axis between the first end 106 and the second end 108) that is between about 80-500 microns. In another example, the body 101 may have a maximum diameter across its length that is between about 80-150 microns. In addition, the body 101 may have a maximum thickness that is between about 20-200 microns, such that the hollow core 104 has a maximum width across its length of between about 20-150 microns. The diameter of the body 101 may also vary along the length of the body 101, for instance, such that the first end 106 has a diameter that is smaller than the diameter of the second end 108 of the perimeter wall 102, vice versa, or a location between the first end 106 and the second end 108 has a wider or smaller diameter than the ends 106, 108.

The apparatus 100 may also include a plurality of holes 110 (only two of the holes have been labeled in FIG. 1A). Although not shown in FIG. 1A, the holes 110 may be provided at spaced intervals along the entire periphery of the perimeter wall 102. In any regard, the plurality of holes 110 are depicted as extending from an exterior surface of the perimeter wall 102 and into the hollow core 104. In this regard, when the apparatus 100 is inserted into a surface of an item of interest, material contained in the item of interest may flow through the holes 110 and into the hollow core 104. The material may flow into the hollow core 104 through capillary forces. Other manners in which the material may flow into the hollow core 104 as well as the configurations of the holes 110 are described in greater detail with respect to FIG. 1B below.

The apparatus 100 may also include a cover 112 that blocks an opening in the hollow core 104 at the first end 106 of the perimeter wall 102. The cover 112 is further depicted as including a pointed tip 114, which may facilitate insertion of the apparatus 100 into an item of interest. The cover 112 may be integrally formed with the perimeter wall 102 or may be attached to the first end 106 of the perimeter wall 102 through use of an adhesive, welding, etc.

Turning now to FIG. 1B, there is shown a cross-sectional side view of the apparatus 100 taken along lines A-A in FIG. 1A, according to an example. As more clearly shown in FIG. 1B, each of the holes 110 is angled with respect to the axis at which the perimeter wall 102 extends. Particularly, the holes 110 are angled such that the openings of the holes 110 at the exterior of the perimeter wall 102 may be at a relatively larger distance from the first end 106 as compared with the openings of the holes 110 at the interior of the perimeter wall 102. In addition, the holes 110 may extend through the entire width of the perimeter wall 102, to thereby expose the hollow core 104 to the external environment through the perimeter wall 102. In this regard, material from an item of interest may be collected into the hollow core 104 through the holes 110.

Also shown in FIG. 1B are a plurality of surface-enhanced spectroscopy (SES) elements 120 positioned in the hollow core 104. SES may include surface-enhanced Raman spectroscopy (SERS), surface-enhanced luminescence detection, surface-enhanced fluorescence detection, or other types of surface-enhanced optically enhanced detection. Although not shown, SES elements 120 may additionally or alternatively be provided in the holes 110 of the apparatus 100. In any regard, the SES elements 120, which may include signal enhancing elements, such as plasmonic nano-particles, nanowires, or other signal enhancing structures, are depicted as being arranged in various ordered or random configurations along an interior surface 116 of the perimeter wall 102. Although not shown, the SES elements 120 may be provided around the circumference of the interior surface 116. In addition, although SES elements 120 have been depicted as being positioned over openings 118 in the interior surface 116 of the holes, the SES elements 120 may be cleared from the openings 118. Thus, for instance, the holes 110 may be formed in the perimeter wall 102 following deposition of the SES elements 120 and the SES elements 120 located at the openings 118 may be removed during or following formation of the holes 110. In addition, or alternatively, the SES elements 120 may be positioned in the hollow core 104 with sufficient spaces between the SES elements 120 to enable analyte collected through the holes 110 to pass between the SES elements 120 positioned at the openings 118 of the holes 110.

The SES elements 120 may one or both of enhance signal scattering and facilitate analyte adsorption. The SES elements 120 may generally enhance sensing operations, such as, surface enhanced Raman spectroscopy (SERS), enhanced photoluminescence, enhanced fluorescence, etc., to be performed on molecules positioned on or near the SES elements 120. In some examples, the SES elements 120 may be functionalized to facilitate adsorption of analyte molecules. For example, surfaces of the SES elements 120 may be functionalized such that a particular class of analytes is attracted and may bond or be preferentially adsorbed onto the SES elements 120.

According to an example, the SES elements 120 include elements, such as plasmonic nanoparticles or nanostructures, which may include plasmon-supporting materials such as but not limited to, gold (Au), silver (Ag), and copper (Cu). The SES elements 120 may have nanoscale surface roughness, which may generally be characterized by nanoscale surface features on the surface of the layer(s) and may be produced spontaneously during deposition of the plasmon-supporting material layer(s). By definition herein, a plasmon-supporting material is a material that facilitates signal scattering and the production or emission of a signal from an analyte on or near the material during spectroscopy. In addition, the SES elements 120, e.g., plasmonic nanostructures, may be deposited into the hollow core 104 through, for instance, physical vapor deposition (PVD), chemical vapor deposition (CVD), sputtering, etc., of metallic material, or self-assembly of pre-synthesized nano-particles. Alternatively, the SES elements 120 may be deposited onto a substrate (not shown), for instance, of a polymer material, a metallic material, a semiconductor material, etc., and the substrate may be inserted into the hollow core 104. According to a particular example, the SES elements 120 are positioned on tips of nano-fingers as discussed in greater detail below with respect to FIGS. 4A-4C.

Turning now to FIG. 2, there is a diagram of an apparatus 200 for performing SES, according to an example. It should be understood that the apparatus 200 depicted in FIG. 2 may include additional components and that some of the components described herein may be removed and/or modified without departing from a scope of the apparatus 200. It should also be understood that the components depicted in FIG. 2 are not drawn to scale and thus, the components may have different relative sizes with respect to each other than as shown therein.

As shown in FIG. 2, the apparatus 200 may include the apparatus 100 for collecting a material to be spectrally analyzed depicted in FIGS. 1A and 1B. The apparatus 200 may also include an illumination source 202, which may emit a beam of illumination 204 (such as a laser beam, an LED beam, or other type of light beam) through a dichroic beam splitter 206. The apparatus 200 is may further include a reflector 208 that is to reflect the illumination beam 204 into the material collecting apparatus 100 to illuminate the SES elements 120 and analyte molecules contained in the material collecting apparatus 100. In this regard, the apparatus 200 may be implemented following collection of the analyte molecules from an item of interest through the holes 110.

Generally speaking, the illumination beam 204 operates as an excitation light on the SES elements 120, which causes near fields around the SES elements 120 to be created. The near fields around the SES elements 120 may couple to analyte molecules (not shown) in the vicinities of the SES elements 120. The metallic nanoparticles (or other plasmonic structures) of the SES elements 120 may also act to enhance the signal emission, e.g., Raman emission, process of the analyte molecules. As a result, scattered light (or other signal) is emitted from the analyte molecules and the emission of the scattered signal 210 is enhanced by the SES elements 120. A portion of the scattered signal 210, which may be emitted in all directions from the analyte molecules near the SES elements 120, may be emitted toward the reflector 208.

According to an example, and as discussed above, the interior surface 116 of the perimeter wall 102, which may also include an interior surface of the cover 112, may be reflective. In this example, the interior surface 116 may enable greater intensities or flux of the illumination beam 204 to be applied onto the SES elements 120 and the scattered signal 210 emitted from the analyte molecules to be directed out of the apparatus 100.

In any regard, the scattered signal 210 may be reflected from the reflector 208 and back to the dichroic beam splitter 206. The dichroic beam splitter 206 may also reflect a portion of the scattered signal 210 toward a spectrometer 212. The spectrometer 212 may include optical elements, such as, slits, gratings, lenses, etc., that allow for the separation and measurement of different wavelengths of light. The spectrometer 212 may also include a detector, e.g., a photomultiplier tube (PMT), a charge-coupled device (CCD), a complementary metal-oxide-semiconductor (CMOS), etc., detector) to measure the intensities of the separated wavelength bands. The measured intensities of the separated wavelength bands may be used to identify the analyte.

Various modifications may be made to the apparatus 200 depicted in FIG. 2 without departing from a scope of the apparatus 200. For instance, the reflector 208 may have a parabolic shape that is to focus the illumination beam 204 into the hollow core 104 of the perimeter wall 102 and/or to focus the scattered signal 210 onto the dichroic beam splitter 206. As another example, instead of or in addition to the use of the reflector 208, an optical fiber (not shown) may be connected to the second end 108 of the apparatus 100 and positioned to receive from and direct light to the dichroic beam splitter 206. In this example, the optical fiber may be connected to the second end 108 of apparatus 100 through use of a fastener, e.g., a sleeve, or the optical fiber may be fused to the second end 108. As a yet further example, various additional optical components, e.g., mirrors, prisms, etc., may be positioned to direct the illumination beam 204 into the hollow core 104 and/or the scattered signal 210 to the spectrometer 212.

Additionally, various modifications may be made to the material collecting apparatus 100 depicted in FIGS. 1A, 1B, and 2 without departing from a scope of the apparatus 100 depicted therein. Examples of the modifications to the material collecting apparatus 100 are depicted herein with respect to the diagrams of the apparatuses depicted in FIGS. 3A-3J. Although the apparatuses depicted in FIGS. 3A-3J are discussed as including various features, it should be clearly understood that the various features depicted therein may be combined in any of multiple combinations without departing to a scope of the apparatus 100 disclosed herein.

With reference first to FIG. 3A, there is shown a cross-sectional side view of an apparatus 300 for collecting a material to be spectrally analyzed, according to an example. The apparatus 300 may include all of the features of the apparatus 100 depicted in FIG. 1B, except for the cover 112 at the first end 106 of the perimeter wall 102. Instead, in the apparatus 300 in FIG. 3A, the hollow core 104 may include a first core opening 302 and a second core opening 304. In one regard, when the apparatus 300 is inserted into an item of interest, material from the item of interest may be collected into the hollow core 104 through the first core opening 302. In addition, if the first core opening 302 becomes blocked or impeded, material from the item of interest may still be collected into the hollow core 104 through the holes 110.

With reference now to FIG. 3B, there is shown a cross-sectional side view of an apparatus 310 for collecting material to be spectrally analyzed, according to another example. The apparatus 310 is depicted as including all of the features of the apparatus 100 depicted in FIG. 3A, except that the apparatus 310 may include a plurality of hollow cores 312. According to an example, each of the hollow cores 312 may have circular cross-sections similar to the hollow core 104 depicted in FIG. 1B, and may include a first core opening 314 and a second core opening 316. The hollow cores 312 may also include SES elements 120. In addition, the holes 110 may extend through the perimeter wall 102 and into respective ones the hollow cores 312 to introduce analyte material into close proximities to the SES elements 120.

According to another example, a hollow core 312, such as a centrally located hollow core 312, may not be in communication with any of the holes 310. In this example, the hollow core 312 that is not in communication with any of the holes 310 may still receive material from an item of interest through a first core opening 314 of that hollow core 312. According to a further example, the first end 106 of the apparatus 310 may include a cover 112 as shown in FIG. 1B.

Turning now to FIG. 3C, there is shown a cross-sectional side view of an apparatus 320 for collecting a material to be spectrally analyzed, according to another example. The apparatus 320 may differ from the apparatus 100 depicted in FIGS. 1B, 3A, and 3B in that the apparatus 320 may not include a hollow core. Instead, the body 101 the apparatus 320 may be formed of a material through which light may relatively easily traverse. That is, the body 301 may be formed of an optically transparent material. In addition, the SES elements 120 may be positioned within the holes 110 in the apparatus 320. In this regard, excitation light may be pumped through the body 301 and onto the SES elements 120 contained in the holes 110.

According to an example, an opaque and/or reflective cladding (not shown) may be provided on an exterior surface of the body 301 to increase the intensity and flux of the excitation light being directed onto the SES elements 120 and the scattered signals emitted from molecules in contact with and/or close proximities to the SES elements 120. In addition, or alternatively, the apparatus 320 may include a cover 112 as shown in FIG. 1B.

Figure 3E:
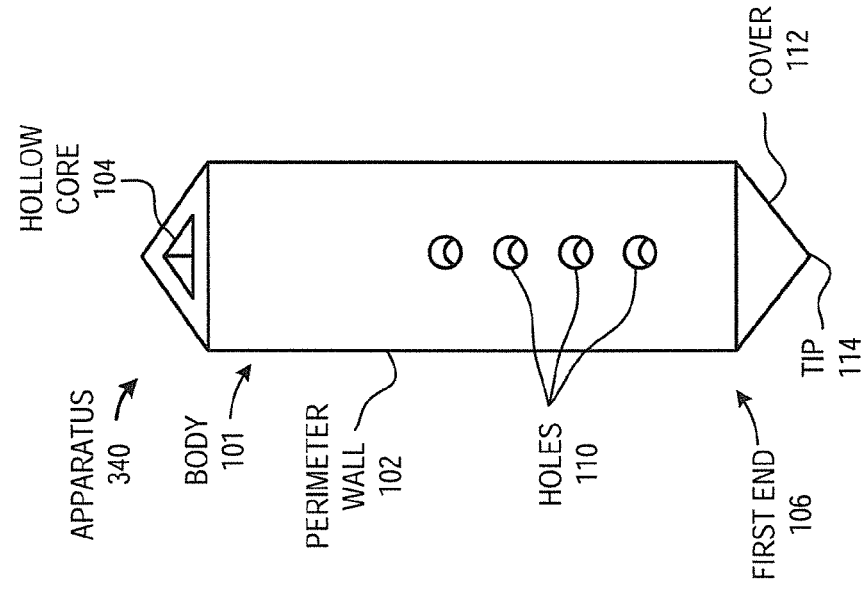
FIGS. 3D and 3E, respectively show perspective views of an apparatus for collecting a material to be spectrally analyzed, according to examples of the present disclosure.
Figure 3D:
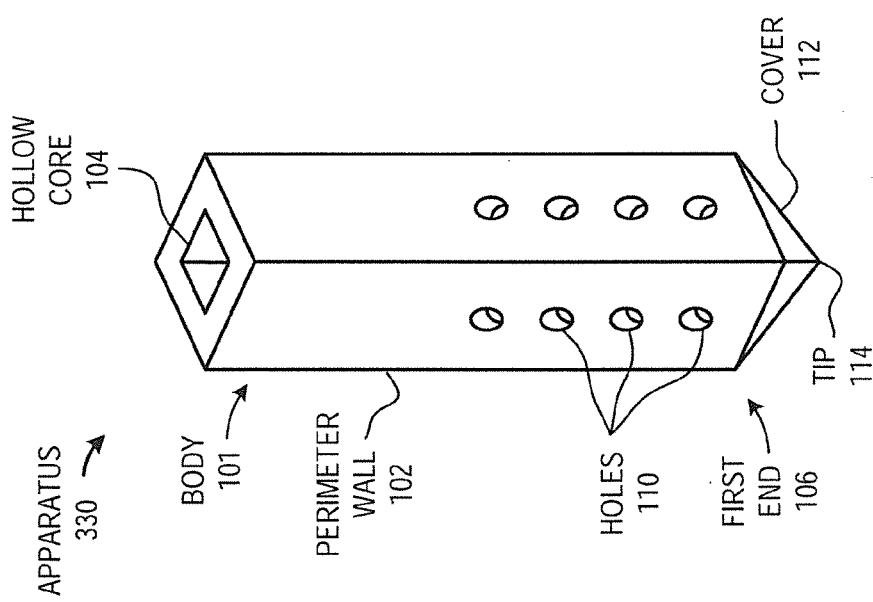

Turning now to FIGS. 3D and 3E, there are respectively shown perspective views of apparatuses 330 and 340 for collecting material to be spectrally analyzed, according to other examples. The apparatuses 330 and 340 are similar to the apparatus 100 depicted in FIG. 1A, but have different cross-sectional shapes as compared to the apparatus 100. That is, the apparatus 330 is depicted as having a square or rectangular cross-section and the apparatus 340 is depicted as having a triangular cross-section. As other examples, however, the apparatus for insertion into an item of interest may include other cross-sectional shapes, such as other polygon shapes, ovals, etc. The apparatus 100 may also have different widths along the longitudinal and/or axial directions, such that the apparatus has a non-uniform cross-section in either or both of the longitudinal and axial directions of the apparatus 100.

Turning now to FIG. 3F, there is shown a cross-sectional side view of an apparatus 350 for collecting a material to be spectrally analyzed, according to another example. The apparatus 350 may differ from the apparatus 100 depicted in FIG. 1B in that the apparatus 350 may include an electrically conductive metal layer 352 on the interior surface 116 of the perimeter wall 102. Particularly, the electrically conductive metal layer 352 is depicted as being provided between the SES elements 120 and the interior surface 116. The electrically conductive metal layer 352 may be provided on the interior surface 116 through any suitable metal deposition technique. For instance, the electrically conductive metal layer 352, which may include Au (gold), Pt (platinum), TiN (titanium oxide), etc., may be deposited using atomic layer deposition (ALD), or other suitable deposition technique. In addition, the electrically conductive metal layer 352 may be a relatively thin coating, for instance, anywhere in the range between about 10 nm-100 nm.

Generally speaking, the electrically conductive metal layer 352 is to generate an electric field through receipt of a voltage, in which the electric field is to enhance attraction of analytes onto the SES elements 120. Although not shown, the electrically conductive metal layer 352 may be divided into separate segments, in which different segments may receive differently biased voltages, such that the electric field may be generated between the different segments of the electrically conductive metal layer 352.

Turning now to FIGS. 3G and 3H, there are shown cross-sectional side views of an apparatus 360 for collecting a material to be spectrally analyzed, according to another example. The apparatus 360 may differ from the apparatus 100 depicted in FIG. 1B in that the apparatus 360 may include a device 362 positioned on the body 101 to controllably reduce a diameter of the body 101. The device 362 may have a pair of bi-metal layers 364, one on each side of the perimeter wall 102. Although not shown, each of the bi-metal layers 364 may wrap around part of the outer circumference of the perimeter wall 102. In this regard each of the bi-metal layers 364 may have curved configurations that substantially match the curvature of the perimeter wall 102.

The bi-metal layers 364 may be fabricated on the perimeter wall 102 through any suitable metal deposition techniques. For instance, the bi-metal layers 364 may be fabricated through evaporation of metals on either side of the perimeter wall 102. In addition, a first layer of each of the bi-metal layers 364 may be formed of a material that has a different thermal coefficient than the second layer of each of the bi-metal layers 364. More particularly, the different thermal coefficients of the first layers and the second layers of each of the bi-metal layers 364 may cause the bi-metal layers 364 to be bent when heat is applied to the bi-metal layers 364. An example of this bending is depicted in FIG. 3H. As shown therein, the bending of the bi-metal layers 364 may generally cause the body 101 to be compressed. In addition, as the bi-metal layers 364 cool down, the body 101 may return to the decompressed configuration depicted in FIG. 3G.

Thus, for instance, the apparatus 360 may be inserted into an item of interest while in the compressed state depicted in FIG. 3H. Following insertion of the item of interest, the bi-metal layers 364 may cool down thus causing the body 101 of the apparatus 360 to return to the decompressed configuration depicted in FIG. 3G. In one regard, therefore, as the bi-metal layers 364 cool down, the pressure inside of the hollow core 104 may increase due to the expansion of the size of the hollow core 104. This increased pressure may enhance collection of the material into the specimen through the holes 110.

Figure 3J:
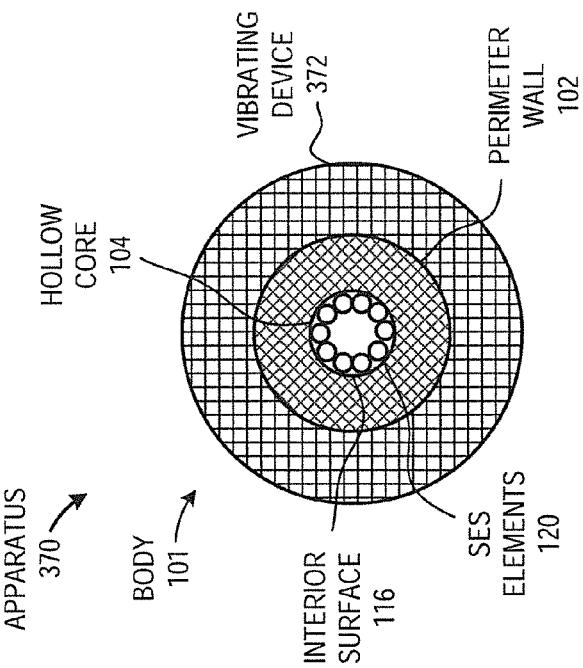
FIG. 3J shows a cross-sectional top view of an apparatus for collecting a material to be spectrally analyzed along lines B-B in FIG. 3I, according to an example of the present disclosure.
Figure 3I:
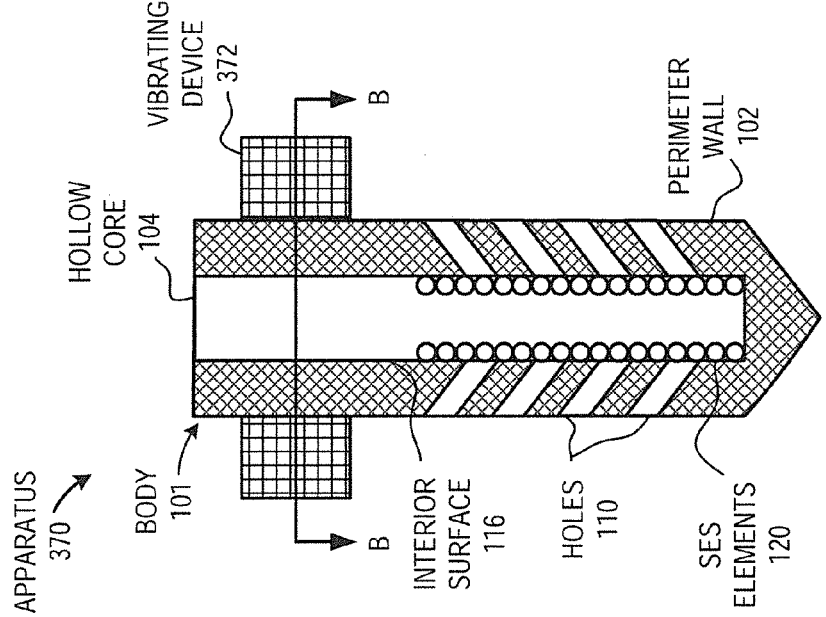

Turning now to FIGS. 3I and 3J, there are respectively shown a cross-sectional side view of an apparatus 370 for collecting a material to be spectrally analyzed and a cross-sectional top view of the apparatus 370 taken along lines B-B in FIG. 3I, according to another example. The apparatus 370 may differ from the apparatus 100 depicted in FIG. 1B in that the apparatus 370 may include a vibrating device 372 in contact with the body 101. Particularly, the vibrating device 372 depicted in FIGS. 3I and 3J may be provided around the body 101.

According to an example, the vibrating device 372 may be formed of a lead zirconate titanate (PZT) material that displays a piezoelectric effect when supplied with a voltage. In one regard, the vibrating device 372 may vibrate the apparatus 370 to enhance penetration of the apparatus 370 into an item of interest and to assist in the collection of analyte through the holes 110.

Figure 4A:
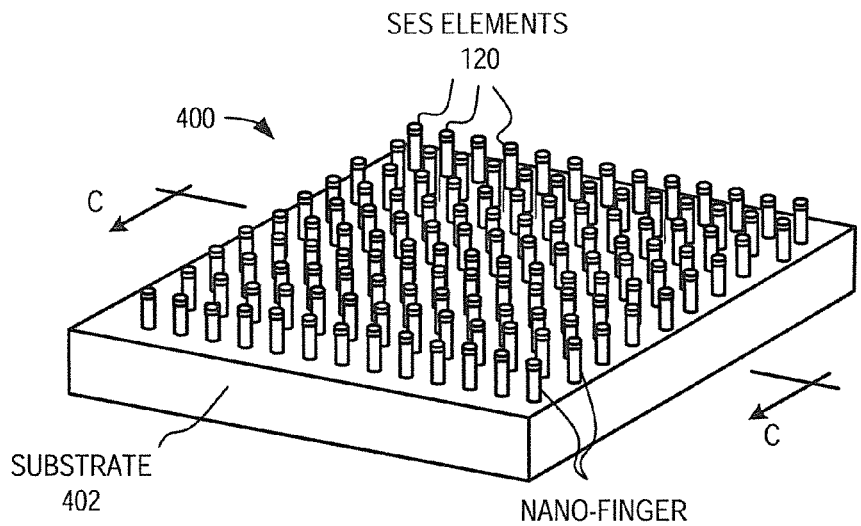
FIG. 4A shows an isometric view of an array of SES elements, in this instance nano-fingers, that may be implemented in the apparatus depicted in FIGS. 1A-3E, according to an example of the present disclosure.
Figure 4B:
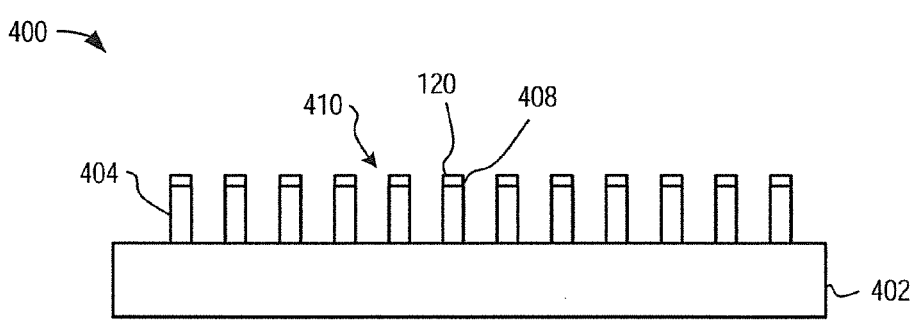
FIGS. 4B and 4C, respectively show cross-sectional views along a line C-C, shown in FIG. 4A, prior to and following collapse of the nano-fingers, according to examples of the present disclosure.
Figure 4C:
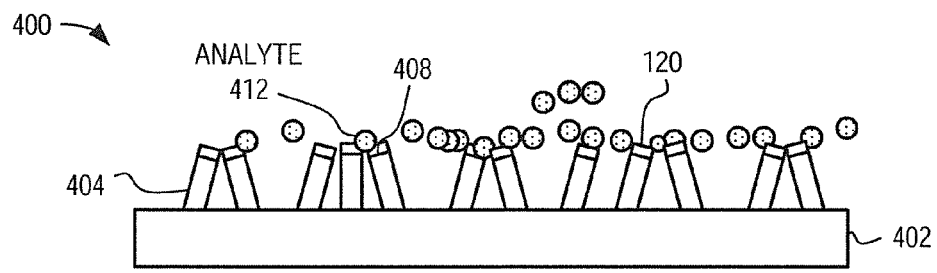

Turning now to FIGS. 4A-4C, there are respectively shown an isometric view and side views of an array 400 of SES elements 120, according to an example. It should be understood that the array 400 depicted in FIGS. 4A-4C may include additional components and that some of the components described herein may be removed and/or modified without departing from a scope of the apparatus for insertion into a surface of an item of interest disclosed herein. It should also be understood that the components depicted in FIGS. 4A-4C are not drawn to scale and thus, the components may have different relative sizes with respect to each other than as shown therein.

Generally speaking, the array 400 depicted in FIGS. 4A-4C includes an example in which the SES elements 120 may be positioned on the tops of nano-fingers 404. As shown in FIG. 4A, the array 400 includes a substrate 402 upon which the nano-fingers 404 extend. More particularly, the nano-fingers 404 may be attached to and extend above a surface of the substrate 402. The substrate 402 may be formed of any suitable material, such as, silicon, silicon nitride, glass, plastic, polymer, $SiO_2$, $Al_2O_3$, aluminum, etc., or a combination of these materials, etc.

According to an example, the nano-fingers 404 may have dimensions that are in the nanometer range, for instance, dimensions that may be less than about 500 nm, and may be formed of a relatively flexible material to enable the nano-fingers 404 to be laterally bendable or collapsible, for instance, to enable tips of the nano-fingers 404 to move toward each other, as discussed in greater detail herein below. Examples of suitable materials for the nano-fingers 404 include polymer materials, such as, UV-curable or thermal curable imprinting resist, polyalkylacrylate, polysiloxane, polydimethylsiloxane (PDMS) elastomer, polyimide, polyethylene, polypropelene, polyurethane, fluoropolymer, etc., or any combination thereof, metallic materials, such as, gold, silver, aluminum, etc., semiconductor materials, etc., and combinations thereof.

The nano-fingers 404 may be attached to the surface of the substrate 402 through any suitable attachment mechanism. For instance, the nano-fingers 404 may be grown directly on the substrate 402 surface through use of various suitable nano-structure growing techniques. As another example, the nano-fingers 404 may be integrally formed with the substrate 402. In this example, for instance, a portion of the material from which the substrate 402 is fabricated may be etched or otherwise processed to form the nano-fingers 404. In a further example, a separate layer of material may be adhered to the substrate 402 surface and the separate layer of material may be etched or otherwise processed to form the nano-fingers 404. In various examples, the nano-fingers 404 may be fabricated through a nanoimprinting or embossing process in which a template of relatively rigid pillars may be employed in a multi-step imprinting process on a polymer matrix to form the nano-fingers 404. In these examples, a template may be formed through photolithography or other advanced lithography with the desired patterning to arrange the nano-fingers 404 in the predetermined arrangement. More particularly, for instance, the desired patterns may be designed on a mold by any of E-beam lithography, photolithography, laser interference lithography, Focused Ion Beam (FIB), self-assembly of spheres, etc. In addition, the pattern may be transferred onto another substrate, for instance, a silicon, glass, or polymer substrate (PDMS, polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 404.

The nano-fingers 404 have been depicted as having substantially cylindrical cross-sections. It should, however, be understood that the nano-fingers 404 may have other shaped cross-sections, such as, for instance, rectangular, square, triangular, etc. In addition, or alternatively, the nano-fingers 404 may be formed with features, such as, notches, bulges, etc., to substantially cause the nano-fingers 404 to be inclined to collapse in particular directions. Thus, for instance, two or more adjacent nano-fingers 404 may include the features to increase the likelihood that the nano-fingers 404 at least partially collapse toward each other. Various manners in which the nano-fingers 404 may be collapsed are described in greater detail herein below.

The array 400 may include a substantially random distribution of nano-fingers 404 or a predetermined configuration of nano-fingers 404. In any regard, according to an example, the nano-fingers 404 may be arranged with respect to each other such that the tips of at least two neighboring nano-fingers 404 may be able to be brought into close proximity with each other when the nano-fingers 404 are in a partially collapsed state. By way of particular example, the neighboring nano-fingers 404 may be positioned less than about 100 nanometers apart from each other. According to a particular example, the nano-fingers 404 may be patterned on the substrate 402 such that neighboring ones of the nano-fingers 404 preferentially collapse into predefined geometries, for instance, triangles, squares, pentagons, etc.

In addition, although FIG. 4A depicts the array 400 as having a relatively large number of nano-fingers 404 arranged along each row, it should be understood that the array 400 may include any number of nano-fingers 404 in each row. In one regard, a relatively large number of nano-fingers 404 may be provided on the substrate 402 to generally enhance the likelihood of detectable light emissions from molecules of an analyte.

The SES elements 120 may include a plasmonic material such as, but not limited to, gold, silver, copper, platinum, aluminum, etc., or a combination of these metals in the form of alloys, or other suitable material that may be able to support surface plasmons for field enhancement for signal scattering. In addition, the SES elements 120 may be multilayer structures, for example, 10 to 100 nm silver layer with 1 to 50 nm gold over-coating, or vice versa. By definition herein, a plasmonic material is a material that supports plasmons. The SES elements 120 may also include other nanostructures and nanoparticles that are coated with a plasmonic material such as metal. In these examples, the SES elements 120 may include, for instance, gold and silver colloidal nanoparticles, black silicon coated with Au or Ag, etc.

Turning now to FIG. 4B, there is shown a cross-sectional view along a line C-C, shown in FIG. 4A, of the array 400, in accordance with an example. As shown therein, each of the tips 408 of the nano-fingers 404 may include a respective SES element 120 disposed thereon. The SES elements 120, which may be metallic nanoparticles, may be deposited onto the tips 408 of the nano-fingers 404 through one of, for instance, physical vapor deposition (PVD), chemical vapor deposition (CVD), sputtering, etc., of metallic material, or self-assembly of pre-synthesized nano-particles.

Although the nano-fingers 404 have been depicted in FIGS. 4A-4B as each extending vertically and at the same heights with respect to each other, it should be understood that some of the nano-fingers 404 may extend at various angles and heights with respect to each other. The differences in angles and/or heights between the nano-fingers 404 may occur, for instance, due to differences arising from manufacturing or growth variances that may be existent in the fabrication of the nano-fingers 404 and the deposition of the SES elements 120 on the nano-fingers 404, etc.

As shown in FIG. 4B, the nano-fingers 404 may be in a first position, in which the tips 408 are in a substantially spaced arrangement with respect to each other. The gaps 410 between the tips 408 may be of sufficiently large size to enable a liquid to be positioned in the gaps 410. In addition, the gaps 410 may be of sufficiently small size to enable the tips 408 of at least some of the nano-fingers 404 to be drawn toward each other as the liquid provided in the gaps 410 evaporates, through, for instance, capillary forces applied on the tips 408 as the liquid evaporates.

Turning now to FIG. 4C, there is shown a cross-sectional view along a line C-C, shown in FIG. 4A, of the array 400, following evaporation of the liquid, according to an example. The view depicted in FIG. 4C may be identical to the view depicted in FIG. 4B, except that the nano-fingers 404 may be in a second position, in which the tips 408 of some of the nano-fingers 404 have been drawn toward with each other. According to an example, the tips 408 of some of the nano-fingers 404 may be in and may remain in relatively close proximity to with each other for a period of time due to the capillary forces applied on adjacent ones of the nano-fingers 404 during and following evaporation of the liquid (not shown) in the gaps 410 between the tips 408. In addition, the SES elements 120 on the adjacent tips 408 may bond to each other through, for instance, gold-gold bonding, binding molecules (not shown), etc.

In any event, and in one regard, the tips 408 of the nano-fingers 404 may be caused to be drawn toward each other as shown in FIG. 4C to enhance signal emission by analyte molecules 412 in the near fields of the SES elements 120 because the relatively small gaps between the SES elements 120 on the adjacent tips 408 create "hot spots" having relatively large electric field strengths. According to an example, the nano-fingers 404 may be positioned into the partially collapsed state depicted in FIG. 4C prior to insertion of the apparatus 100 into a surface of an item of interest.

According to an example, the SES elements 120 depicted in FIGS. 4A-4C may be formed on the substrate 402 and the substrate 402 may be inserted into the apparatus 100. For instance, the array 400, including both the SES elements 120 and the substrate 402, may be inserted into the hollow core 104 and/or the holes 110 of the apparatus 100. The array 400 may also be attached to an interior surface of the perimeter wall 102, for instance, through use of an adhesive.

In another example, the SES elements 120 depicted in FIGS. 4A-4C may be formed directly on an interior surface 116 of the perimeter wall 102 (and/or the holes 110) instead of first being formed on the substrate 402. In this example, the perimeter wall 102 may include a material and structure that is able to be in a relatively flat state and a relatively curved state. As such, the SES elements 120 may be formed on the perimeter wall 102 while the perimeter wall 102 is in the relatively flat state and the perimeter wall 102 may be caused to obtain the relatively curved state following formation of the SES elements 120. The perimeter wall 102 in this example may be formed of a material and structure that is to automatically move from the relatively flat state to the relatively curved state to application of an external stimulus, which may include a chemical stimulus, an electrical stimulus, a thermal stimulus, a physical stimulus, etc. Examples of materials that may be used to form the perimeter wall 102 may include titanium-palladium-nickel, nickel-titanium-copper, gold-cadmium, iron-zinc-copper-aluminium, titanium-niobium-aluminium, uranium-niobium, hafnium-titanium-nickel, iron-manganese-silicon, nickel-titanium, nickel-iron-zinc-aluminium, copper-aluminium-iron, titanium-niobium, zirconium-copper-zinc, nickel-zirconium-titanium, etc.

Turning now to FIGS. 4D and 4E, there are shown cross-sectional side views of an apparatus 380 for collecting a material to be spectrally analyzed, according to another example. The apparatus 380 may differ from the apparatus 100 depicted in FIG. 1B in that in the apparatus 380, a plurality of nano-fingers 404 may be positioned on a bottom of the interior surface 116. The bottom of the interior surface 116 may be a side of the cover 112 that is opposite the tip 114 on the cover 112. The nano-fingers 404 may be positioned on the bottom of the interior surface 116 or alternatively, the top of the cover 112, in any of the manners discussed above with respect to FIG. 4A. In addition, the SES elements 120 may be positioned on tops of nano-fingers 404. By way of example, the nano-fingers 404 and the SES elements 120 may be provided on the cover 112 and the cover 112 may then be attached to the body 101.

Moreover, the nano-fingers 404 are depicted in FIG. 4E as being in a partially collapsed configuration such that some of the SES elements 120 are in contact with other SES elements 120 as discussed above with respect to FIG. 4C. In one regard, when the SES elements 120 positioned on the nano-fingers 404 are illuminated, a radiation pattern may be formed that is relatively sharp, directional, and couples well to the optical modes of the apparatus 380, which may substantially enhance the signal emitted out of the apparatus 380. According to an example, the bottom of the interior surface 116 may have an optically reflective surface as discussed above, to also enhance the radiation pattern formed above the SES elements 120.

Figure 5:
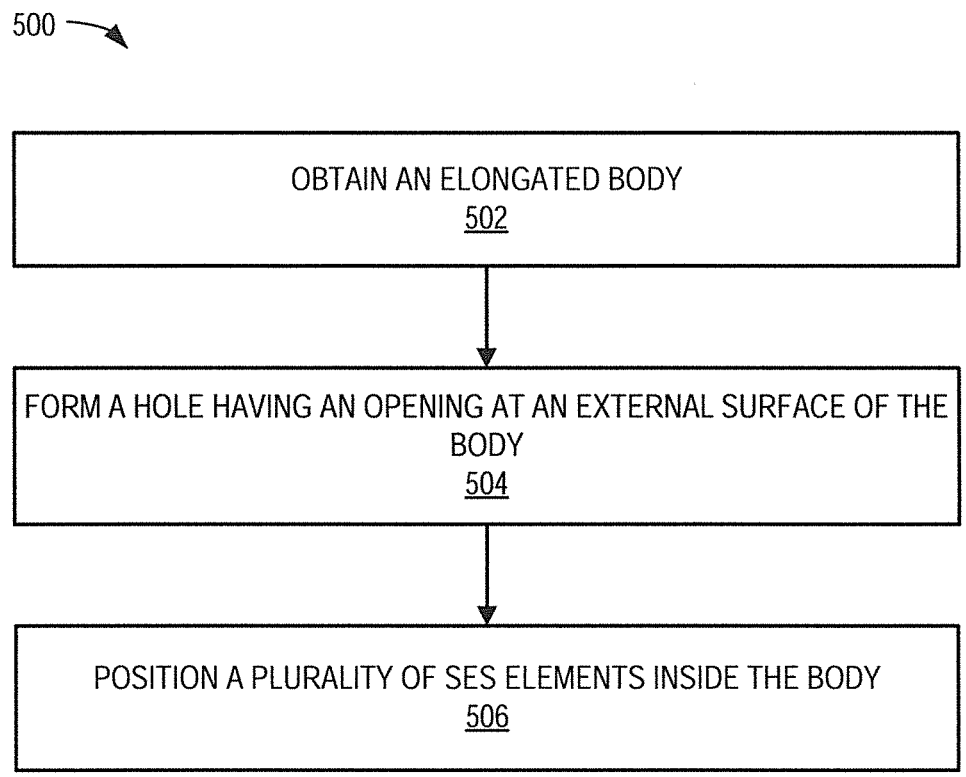
FIG. 5 shows a flow diagram of a method for fabricating an apparatus for collecting material from an item of interest to be spectrally analyzed, according to an example of the present disclosure.

Turning now to FIG. 5, there is shown a flow diagram of a method 500 for fabricating an apparatus 100 for collecting material from an item of interest to be spectrally analyzed, according to an example. It should be understood that the method 500 depicted in FIG. 5 may include additional processes and that some of the processes described herein may be removed and/or modified without departing from a scope of the method 500. In addition, although particular reference is made herein to the apparatus 100 as being fabricated through implementation of the method 500, it should be understood that the method 500 may be implemented to fabricate a differently configured apparatus, such as any of the other apparatuses 300, 310, 320, 330, and 340 disclosed herein, without departing from a scope of the method 500.

At block 502, a body 101 having a first end 106 and a second end 108, in which the body 101 is elongated along a first axis from the first end 106 to the second end 108 may be obtained. The body 101 may include a perimeter wall 102, in which the interior surface 116 of the perimeter wall 102 may form a hollow core 104 as shown, for instance, in FIGS. 1A and 1B. Alternatively, the body 101 may include a solid structure as shown, for instance, in FIG. 3C. In addition, the body 101 may include any of a variety of cross-sectional shapes as also discussed above with respect to FIGS. 3A-3E. As a further alternative, the body 101 may include a relatively flat or curved configuration that is to be folded or curled such that a surface the body 101 forms a hollow core 104.

At block 504, a hole 110 (or holes 110) may be formed, in which the hole(s) 110 may have an opening at an external surface of the body 101 at a location between the first end 106 and the second end 108 and may extend at least partially through the body 101 at an angle with respect to the first axis. According to an example, the hole(s) 110 may be formed to have an opening 118 at the interior surface 116 of the perimeter wall 102, for instance, as shown in FIG. 1B. According to another example, the hole(s) 110 may be formed such that an end of the hole(s) 110 opposite the opening at the external surface of the body 101 is closed, for instance, as shown in FIG. 3C. In either example, the hole(s) 110 may be formed such that the opening(s) of the hole(s) 110 opposite the opening(s) at the external surface of the body 101 is in closer proximity to the first end 106 than the opening(s) at the external surface of the body 101.

The hole(s) 110 may be formed in the body 101 through implementation of any suitable fabrication technique. For instance, the hole(s) 110 may be formed in the body 101 through use of etching techniques, drilling techniques, etc.

At block 506, a plurality of SES elements 120 may be positioned inside the body 101. The SES elements 120 may be positioned inside the body 101 through any of the manners discussed above. In addition, the SES elements 120 may be positioned in either or both of a hollow core 104 and the hole(s) 110 of the body 101. According to an example, the SES elements 120 may be positioned inside of the hollow core 104 prior to formation of the hole(s) 110 in the perimeter wall 102 at block 504. In this example, the openings in the SES elements 120 may be formed to enable analyte material to be introduced into the hollow core 104 through the hole(s) 110.

In an example in which the body 101 may include a relatively flat or curved configuration that is to be folded or curled, the SES elements 120 may be positioned on a surface of the body 101 prior to the body 101 being folded or curled. In addition, the hole(s) 110 may be formed in the body 101 at any time during the fabrication of the apparatus 100. The apparatus 100 may additionally be fabricated to include any of the additional features discussed above.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for collecting a material to be spectrally analyzed, said apparatus comprising:
    a body having a perimeter wall and a hollow core, said perimeter wall having a first end and a second end;
    a cover positioned on the first end of the perimeter wall to block an end of the hollow core, said cover having a conical tip extending away from the perimeter wall and a reflective surface on a side of the cover opposite the conical tip, wherein the body is elongated along a first axis from the first end to the second end and wherein the conical tip is to be inserted through a surface of an item of interest;
    a hole having a first opening formed in an external surface of the perimeter wall and a second opening formed at an interior of the perimeter wall, wherein the second opening is closer to the first end of the perimeter wall than the first opening; and
    a plurality of surface-enhanced spectroscopy (SES) elements positioned inside the hollow core.

2. The apparatus according to claim 1, wherein the hollow core is formed by an interior surface of the perimeter wall and extends along the first axis.

3. The apparatus according to claim 2, wherein the hollow core extends from the first end to the second end of the body.

4. The apparatus according to claim 2, wherein the plurality of SES elements are positioned in the hole, the hollow core, or both the hole and the hollow core.

5. The apparatus according to claim 2, further comprising:
    a metal layer provided on the interior surface of the perimeter wall, wherein the metal layer is to receive a voltage to enhance attraction of an analyte onto the SES elements.

6. The apparatus according to claim 1, wherein the body has a maximum diameter perpendicular to the first axis of between about 80-500 microns.

7. The apparatus according to claim 1, further comprising:
    a device positioned on the body to controllably reduce a diameter of the body.

8. The apparatus according to claim 1, further comprising:
    a vibrating device in contact with the body to cause the body to vibrate.

9. The apparatus according to claim 1, wherein the perimeter wall surrounds a plurality of hollow cores, wherein each of the plurality of hollow cores extends along the first axis, and wherein the second opening connects to at least one of the plurality of hollow cores.

10. The apparatus according to claim 1, wherein the body is formed of an optically transparent material.

11. The apparatus according to claim 1, further comprising:
    a plurality of nano-fingers extending from a surface inside of the body, wherein the plurality of SES elements are positioned on tips of the plurality of nano-fingers.

12. An apparatus for performing surface-enhanced spectroscopy (SES), said apparatus comprising:
    a probe having,
        a body having perimeter wall and a hollow core, said perimeter wall having a first end and an opposite a second end;
        a cover positioned on the first end of the perimeter wall to block an end of the hollow core, said cover having a conical tip extending away from the perimeter wall and a reflective surface on a side of the cover opposite the conical tip, wherein the body is elongated along a first axis from the first end to the second end and wherein the conical tip is to be inserted through a surface of an item of interest;
        a hole having an a first opening formed in an external surface of the perimeter wall and a second opening formed at an interior of the perimeter wall, wherein the second opening is closer to the first end of the perimeter wall than the first opening; and
        a plurality of surface-enhanced spectroscopy (SES) elements positioned inside the hollow core;

an illumination source in communication with the second end of the body to illuminate the plurality of SES elements; and a detector positioned to detect light emitted from an analyte positioned near the plurality of SES elements.

13. The apparatus according to claim 12, wherein the hollow core is formed by an interior surface of the perimeter wall and extends along the first axis from the first end to the second end of the body.

14. A method for fabricating an apparatus for collecting material from an item of interest to be spectrally analyzed, the method comprising:

obtaining a body having a perimeter wall and a hollow core, said perimeter wall having a first end and a second end;

a cover positioned on the first end of the perimeter wall to block an end of the hollow core, said cover having a conical tip extending away from the perimeter wall and a reflective surface on a side of the cover opposite the conical tip, wherein the body is elongated along a first axis from the first end to the second end and wherein the conical tip is to be inserted through a surface of an item of interest;

forming a hole having a first opening at an external surface of the perimeter wall and a second opening formed at an interior of the perimeter wall, wherein the second opening is closer to the first end of the perimeter wall than the first opening; and positioning a plurality of surface-enhanced spectroscopy (SES) elements inside the hollow core.

* * * * *

UNITED STATES PATENT AND TRADEMARK OFFICE
CERTIFICATE OF CORRECTION

PATENT NO. : 9,097,616 B2  
APPLICATION NO. : 13/750848  
DATED : August 4, 2015  
INVENTOR(S) : Shih-Yuan Wang et al.

Page 1 of 1

It is certified that error appears in the above-identified patent and that said Letters Patent is hereby corrected as shown below:

In the Claims:

In column 14, line 61, in Claim 12, delete "an a" and insert -- a --, therefor.

Signed and Sealed this
Twenty-first Day of June, 2016

Michelle K. Lee
*Director of the United States Patent and Trademark Office*